(12) United States Patent
Yamada et al.

(10) Patent No.: US 9,746,433 B2
(45) Date of Patent: Aug. 29, 2017

(54) X-RAY FLUORESCENCE SPECTROMETER AND X-RAY FLUORESCENCE ANALYZING METHOD

(71) Applicant: RIGAKU CORPORATION, Akishima-shi, Tokyo (JP)

(72) Inventors: Takashi Yamada, Takatsuki (JP); Yuichiro Shimizu, Takatsuki (JP)

(73) Assignee: Rigaku Corporation, Akishima-shi, Tokyo (JP)

( * ) Notice: Subject to any disclaimer, the term of this patent is extended or adjusted under 35 U.S.C. 154(b) by 0 days.

(21) Appl. No.: 15/391,156

(22) Filed: Dec. 27, 2016

(65) Prior Publication Data

US 2017/0108424 A1    Apr. 20, 2017

Related U.S. Application Data

(63) Continuation of application No. PCT/JP2015/063892, filed on May 14, 2015.

(30) Foreign Application Priority Data

Jul. 1, 2014   (JP) ................................. 2014-135613

(51) Int. Cl.
   *G01N 15/02*   (2006.01)
   *G01N 23/223*   (2006.01)

(52) U.S. Cl.
   CPC ....... *G01N 23/223* (2013.01); *G01N 15/0211* (2013.01); *G01N 15/02* (2013.01);
   (Continued)

(58) Field of Classification Search
   CPC ...... G01N 23/00; G01N 23/22; G01N 23/223; G01N 2223/00; G01N 2223/07;
   (Continued)

(56) References Cited

U.S. PATENT DOCUMENTS

| 4,134,012 A | 1/1979 | Smallbone et al. |
| 5,249,216 A | 9/1993 | Ohsugi et al. |
(Continued)

FOREIGN PATENT DOCUMENTS

| DE | 28 44 704 A1 | 4/1979 |
| JP | 8-327566 A | 12/1996 |
(Continued)

OTHER PUBLICATIONS

International Search Report for PCT/JP2015/063892 dated Aug. 11, 2015 [PCT/ISA/210].
Written Opinion for PCT/JP2015/063892 dated Aug. 11, 2015 [PCT/ISA/237].
(Continued)

*Primary Examiner* — Anastasia Midkiff
(74) *Attorney, Agent, or Firm* — Sughrue Mion, PLLC

(57) ABSTRACT

An X-ray fluorescence spectrometer includes: an X-ray source (3) to irradiate, with primary X-rays (6), a sample (1) that is multiple nanoparticles placed on a substrate (10); an irradiation angle adjustment unit (5) to adjust an irradiation angle at which a surface (10*a*) of the substrate is irradiated; a detection unit (8) to measure an intensity of fluorescent X-rays (7) from the sample (1); a peak position calculation unit (11) to generate a sample profile representing change of the intensity of the fluorescent X-rays (7) against change of the irradiation angle, and to calculate a peak irradiation angle position; a particle diameter calibration curve generation unit (21) to generate a calibration curve; and a particle diameter calculation unit (22) to calculate a particle diameter of nanoparticles of an unknown sample (1) by applying the peak irradiation angle position of the unknown sample (1) to the calibration curve.

7 Claims, 4 Drawing Sheets

(52) U.S. Cl.
CPC ............... *G01N 2223/076* (2013.01); *G01N 2223/3037* (2013.01); *G01N 2223/641* (2013.01)

(58) Field of Classification Search
CPC ......... G01N 2223/076; G01N 2223/10; G01N 2223/101; G01N 2223/1016; G01N 2223/30; G01N 2223/303; G01N 2223/3037; G01N 2223/304; G01N 2223/641; G01N 2223/645; G01N 2223/646; G01N 2223/6462; G01N 2223/6466; G01N 15/02; G01N 15/0205; G01N 15/0211
See application file for complete search history.

(56) References Cited

U.S. PATENT DOCUMENTS

| | | | |
|---|---|---|---|
| 5,742,658 | A | 4/1998 | Tiffin et al. |
| 7,680,243 | B2 | 3/2010 | Yokhin et al. |
| 2009/0067573 | A1 | 3/2009 | Yokhin et al. |

FOREIGN PATENT DOCUMENTS

| | | |
|---|---|---|
| JP | 2003-202306 A | 7/2003 |
| JP | 2010-054334 A | 3/2010 |
| JP | 2010-071762 A | 4/2010 |

OTHER PUBLICATIONS

Communication dated Feb. 7, 2017 from the German Patent and Trademark Office in counterpart Application No. 11 2015 003 094.8.

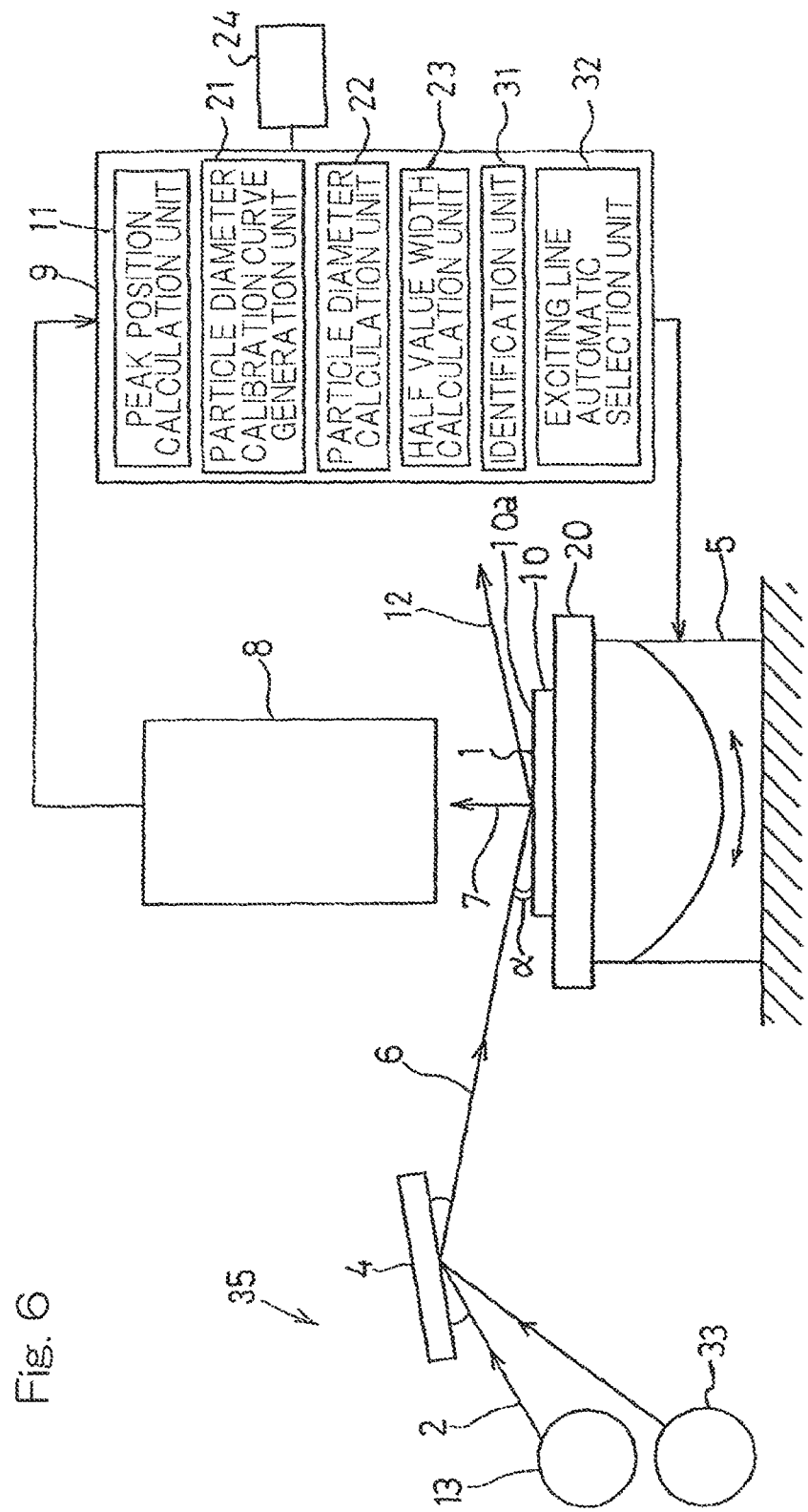

X-RAY FLUORESCENCE SPECTROMETER AND X-RAY FLUORESCENCE ANALYZING METHOD

CROSS REFERENCE TO THE RELATED APPLICATION

This application is a continuation application, under 35 U.S.C. §111(a), of international application No. PCT/JP2015/063892, filed May 14, 2015, which claims priority to Japanese patent application No. 2014-135613, filed Jul. 1, 2014, the entire disclosure of which is herein incorporated by reference as a part of this application.

BACKGROUND OF THE INVENTION (Field of the Invention)

The present invention relates to an X-ray fluorescence spectrometer and an X-ray fluorescence analyzing method that measure the particle diameters of nanoparticles.

(Description of Related Art)

In recent years, application of nanoparticles to, for example, an industrial field and a medical field, is becoming widespread, and management of the particle diameters of nanoparticles is becoming important. The particle diameters of nanoparticles may be measured by a measuring method using an electron microscope, X-ray small angle scattering, or the like. However, in such a measuring method, labor and time are required for preparing samples, and the measurement cannot be simplified. Further, in X-ray small angle scattering, the measurement is performed in a state where nanoparticles float in solvent, and there is a problem that, if the concentration of nanoparticles in solvent is low, the measurement cannot be performed.

Meanwhile, there is an X-ray fluorescence spectrometer that can quantitatively determine, by using the FP method (Fundamental parameter method), all of the composition, the height, and the population of island structures scattered on a substrate (for example, see Patent Document 1.).

For X-ray fluorescence analysis using a calibration curve method, there is a conventional art in which the height of a particulate contamination on a substrate, and a film thickness of the particulate contamination thereon in the case of the particulate contamination being assumed as a film, are determined according to dependence of an intensity of fluorescent X-rays on an incident angle (for example, see Patent Document 2.).

RELATED DOCUMENT

Patent Document

[Patent Document 1] JP Laid-open Patent Publication No. 2010-054334

[Patent Document 2] JP Laid-open Patent Publication No. H08-327566

However, in the techniques disclosed in Patent Documents 1 and 2, the particle diameters of the nanoparticles on the substrate cannot be measured.

SUMMARY OF THE INVENTION

The present invention is made in view of the problem of the conventional art, and an object of the present invention is to provide an X-ray fluorescence spectrometer and an X-ray fluorescence analyzing method capable of simply measuring the particle diameters of nanoparticles on a substrate in a nondestructive manner with easy preprocessing.

In order to attain the above object, an X-ray fluorescence spectrometer of the present invention includes: an X-ray source configured to irradiate, with primary X-rays, a sample that is multiple nanoparticles placed on a substrate; an irradiation angle adjustment unit configured to adjust an irradiation angle at which a surface of the substrate is irradiated with the primary X-rays; a detection unit configured to measure an intensity of fluorescent X-rays generated from the sample; a peak position calculation unit configured to measure, by using the detection unit, an intensity of the fluorescent X-rays generated from the sample each time the irradiation angle is adjusted by the irradiation angle adjustment unit, generate a sample profile representing change of the intensity of the fluorescent X-rays against change of the irradiation angle, and calculate a peak irradiation angle position at which the fluorescent X-rays indicate a highest intensity in the sample profile; a particle diameter calibration curve generation unit configured to generate a calibration curve for a plurality of standard samples each of which includes nanoparticles having a known uniform particle diameter, and among which the uniform particle diameter is different, the calibration curve representing a correlation between the peak irradiation angle position calculated by the peak position calculation unit and the particle diameter of the nanoparticles; and a particle diameter calculation unit configured to calculate a particle diameter of nanoparticles of an unknown sample by applying the peak irradiation angle position calculated for the unknown sample by the peak position calculation unit, to the calibration curve generated by the particle diameter calibration curve generation unit.

The X-ray fluorescence spectrometer of the present invention generates a calibration curve representing correlation between the peak irradiation angle positions and the particle diameters of the nanoparticles, applies the peak irradiation angle position of the unknown sample to the calibration curve, and calculates the particle diameter of the nanoparticles placed on the substrate, whereby the measurement can be simply performed in a nondestructive manner with easy preprocessing.

The X-ray fluorescence spectrometer of the present invention preferably includes a display unit configured to display a warning when the particle diameter of the nanoparticles of the unknown sample is outside a predetermined particle diameter range of the calibration curve. In this case, a person who makes the measurement can be made aware that reliability of a calculated value of the particle diameter is reduced when the particle diameter is outside a predetermined particle diameter range of the calibration curve. When the particle diameter for the unknown sample becomes small, the peak intensity of the sample profile is rapidly reduced, and an error in the calculated value of the particle diameter is increased. Meanwhile, when the particle diameter becomes large, the gradient of the calibration curve becomes gentle, and error in the calculated value of the particle diameter is increased.

The X-ray fluorescence spectrometer of the present invention preferably includes a half value width calculation unit configured to calculate a half value width of the sample profile generated by the peak position calculation unit; and a display unit configured to display a warning when the half value width calculated for the unknown sample by the half value width calculation unit is greater than a predetermined upper limit half value width. The sample profile of a sample in which particles having different particle diameters are mixed, is obtained by overlapping of the sample profiles of particles having the particle diameters, respectively. Therefore, the width of the sample profile is increased. In this case, when the half value width of the sample profile is greater than a predetermined upper limit half value width, the warning is displayed by the display unit. Therefore, a person who makes the measurement can be made aware that the particle diameters are not uniform.

The X-ray fluorescence spectrometer of the present invention preferably includes an identification unit configured to identify an element of nanoparticles of a sample, and an exciting line automatic selection unit configured to automatically select, as the primary X-rays, exciting line corresponding to the element identified by the identification unit. In this case, the element of the nanoparticles of the unknown sample can be efficiently excited, and measurement accuracy can be improved.

An X-ray fluorescence analyzing method of the present invention includes: preparing: an X-ray source configured to irradiate, with primary X-rays, a sample that is multiple nanoparticles placed on a substrate; an irradiation angle adjustment unit configured to adjust an irradiation angle at which a surface of the substrate is irradiated with the primary X-rays; a detection unit configured to measure an intensity of fluorescent X-rays generated from the sample; and a plurality of standard samples each of which includes nanoparticles having a known uniform particle diameter, and among which the uniform particle diameter is different; irradiating each standard sample with the primary X-rays for which an irradiation angle is adjusted by using the irradiation angle adjustment unit, and measuring, by the detection unit, an intensity of fluorescent X-rays generated from the standard sample each time the irradiation angle is adjusted; generating a sample profile representing change of the intensity of the fluorescent X-rays against change of the irradiation angle, and calculating a peak irradiation angle position at which the fluorescent X-rays indicate a highest intensity in the sample profile; generating a particle diameter calibration curve representing a correlation between the peak irradiation angle position calculated for each standard sample, and the particle diameter of the nanoparticles.

The X-ray fluorescence analyzing method of the present invention further includes: preparing an unknown sample; irradiating the unknown sample with the primary X-rays for which an irradiation angle is adjusted by using the irradiation angle adjustment unit, and measuring, by the detection unit, an intensity of fluorescent X-rays generated from the unknown sample each time irradiation is performed; generating a sample profile representing change of the intensity of the fluorescent X-rays against change of the irradiation angle, and calculating a peak irradiation angle position at which the fluorescent X-rays indicate a highest intensity in the sample profile; and calculating a particle diameter of nanoparticles of the unknown sample by applying the peak irradiation angle position calculated for the unknown sample, to the particle diameter calibration curve.

In the X-ray florescence analyzing method, a calibration curve representing correlation between the peak irradiation angle positions and the particle diameters of the nanoparticles is generated, the peak irradiation angle position of the unknown sample is applied to the calibration curve, and the particle diameter of the nanoparticles placed on the substrate is calculated, whereby the measurement can be simply performed in a nondestructive manner with easy preprocessing.

In the X-ray fluorescence analyzing method of the present invention, an element of nanoparticles of a sample is preferably identified, and exciting line corresponding to the identified element is preferably selected as the primary X-rays. In this case, the element of the nanoparticles of the unknown sample can be efficiently excited, and measurement accuracy can be improved.

In the X-ray fluorescence analyzing method of the present invention, samples which include nanoparticles having particle diameters of 1 nm to 100 nm are preferably analyzed. In this case, the particle diameter of the nanoparticles can be obtained with enhanced accuracy. In the specification of the present invention, the sample includes the standard sample and the unknown sample.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims.

In the accompanying drawings, like reference numerals are used to denote like parts throughout the several views, and:

FIG. 6 schematically illustrates an X-ray fluorescence spectrometer according to a second embodiment of the present invention.

DESCRIPTION OF EMBODIMENTS

Figure 1:
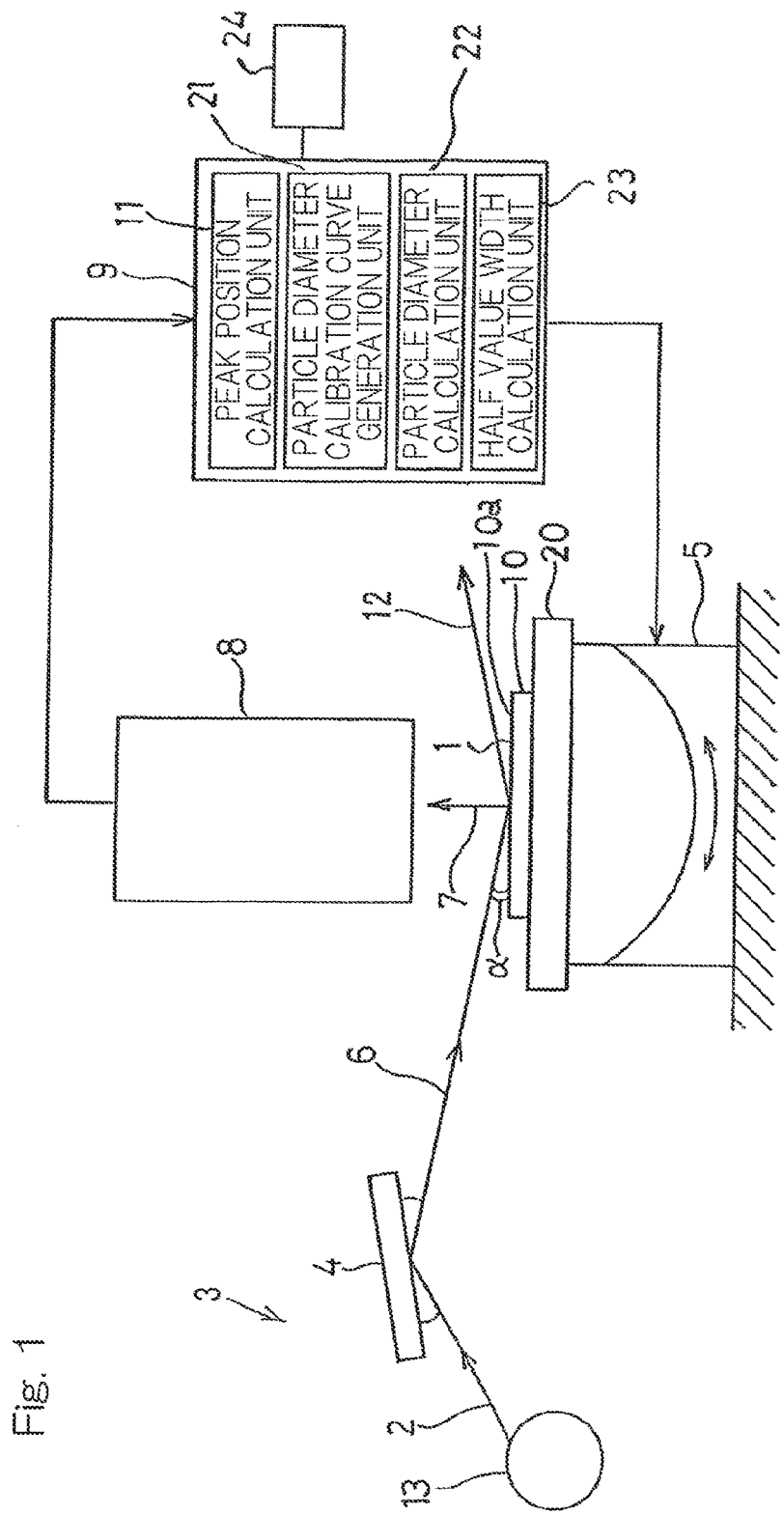
FIG. 1 schematically illustrates an X-ray fluorescence spectrometer according to a first embodiment of the present invention.

Hereinafter, an X-ray fluorescence spectrometer according to a first embodiment of the present invention will be described with reference to the drawings. As shown in FIG. 1, the X-ray fluorescence spectrometer includes: an X-ray source 3 that irradiates, with primary X-rays 6, a sample 1 that is multiple nanoparticles placed on a substrate 10; a detection unit 8 that measures an intensity of fluorescent X-rays 7 generated from the sample 1; and an irradiation angle adjustment unit 5 that adjusts an irradiation angle α at which a surface 10a of the substrate is irradiated with the primary X-rays 6. The detection unit 8 is, for example, a semiconductor detector such as an SDD or an SSD, and is preferably an SDD that can perform counting at up to a high counting rate.

Figure 2:
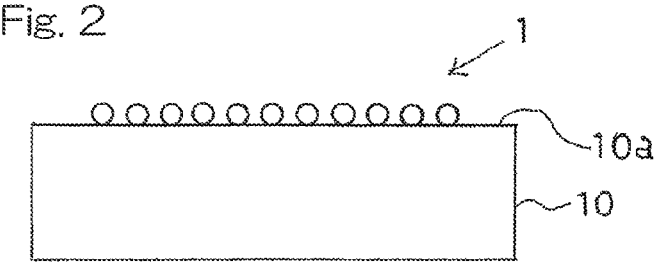
FIG. 2 illustrates an example of a sample to be analyzed by the spectrometer.

As shown in FIG. 2, the sample 1 is, for example, multiple nanoparticles 1 placed on the substrate 10 that is a silicon wafer, and the nanoparticles are scattered on the substrate 10. The substrate 10 on which the sample 1 is placed, is mounted onto a sample table 20 (FIG. 1). The nanoparticles 1 are preferably placed on the surface 10a of the substrate so as to be uniformly distributed.

As shown in FIG. 1, the X-ray source 3 includes: an X-ray tube 13 that generates X-rays 2 from a target; and a spectroscopic device 4 that monochromates the X-rays 2 generated from the X-ray tube 13. The X-rays monochromated by the spectroscopic device 4 are the primary X-rays 6 with which the sample 1 is irradiated. The X-ray tube 13 is, for example, a molybdenum X-ray tube. The X-ray fluorescence spectrometer is a grazing incidence X-ray fluorescence spectrometer, and the primary X-rays 6 are incident on the substrate surface 10a at a very small irradiation angle α that is, for example, less than or equal to 1 degree such that, for example, most of the primary X-rays become reflected X-rays 12, that is, a so-called total reflection phenomenon is caused. The irradiation angle α is adjusted by the irradiation angle adjustment unit 5 such as a swivel stage provided below the sample table 20.

The X-ray fluorescence spectrometer includes control unit 9 that is implemented as a computer that includes a peak position calculation unit 11, a particle diameter calibration curve generation unit 21, a particle diameter calculation unit 22, a half value width calculation unit 23, and a display unit 24 as described below. The control unit 9 drives the irradiation angle adjustment unit 5 to adjust an irradiation angle α. The peak position calculation unit 11 measures, by using the detection unit 8, an intensity of the fluorescent X-rays 7 generated from the sample 1 each time the irradiation angle for the primary X-rays 6 is adjusted by the irradiation angle adjustment unit 5, generates a sample profile representing change of an intensity of the fluorescent X-rays 7 against change of the irradiation angle, and calculates a peak irradiation angle position at which the fluorescent X-rays 7 indicate the highest intensity in the sample profile.

For a plurality of standard samples 1 each of which includes the nanoparticles 1 having a known uniform particle diameter, and among which the uniform particle diameter is different, the particle diameter calibration curve generation unit 21 generates a calibration curve representing correlation between the peak irradiation angle positions calculated by the peak position calculation unit 11 and the particle diameters of the nanoparticles 1. The particle diameter calculation unit 22 calculates, for an unknown sample 1, the particle diameter of the nanoparticles 1 by applying the peak irradiation angle position calculated for the unknown sample 1 by the peak position calculation unit 11, to the calibration curve generated by the particle diameter calibration curve generation unit 21.

The display unit 24 displays a warning indicating that "the particle diameter is outside a predetermined particle diameter range and reliability is low", if the particle diameter of the nanoparticles 1 in the unknown sample 1 is outside a predetermined particle diameter range of the calibration curve, for example, a range of 5 nm to 80 nm. The predetermined particle diameter range can be determined as appropriate according to, for example, variation, in particle diameter, which is calculated by the particle diameter calculation unit 22 through repeated measurement of the standard sample 1 or a sample 1 which includes similar particles having a known uniform particle diameter.

The half value width calculation unit 23 calculates a half value width of the sample profile generated by the peak position calculation unit 11, and causes the display unit 24 to display a warning indicating that "a predetermined amount or more of particles having different particle diameters are contained", for example, together with the calculated particle diameter or instead of the calculated particle diameter, if the half value width calculated for the unknown sample 1 is greater than a predetermined upper limit half value width. An operation performed by the half value width calculation unit 23 will be described below in detail.

Next, an operation performed by the X-ray fluorescence spectrometer according to the first embodiment of the present invention will be described. A plurality of the standard samples 1 each of which includes the nanoparticles 1 having a known uniform particle diameter, and among which the uniform particle diameter is different, are prepared. For example, the standard samples 1 in which the multiple nanoparticles 1 of gold on the substrate 10 have particle diameters of 5 nm (nanometers), 10 nm, 20 nm, 30 nm, 50 nm, and 100 nm, respectively, are prepared. Firstly, the standard sample 1 for the particle diameter of 5 nm is placed on the sample table 20 (FIG. 1), and the standard sample 1 for the particle diameter of 5 nm is irradiated with the primary X-rays 6, and the intensity of the fluorescent X-rays 7 generated from the standard sample 1 for the particle diameter of 5 nm is measured by the detection unit 8 each time the irradiation angle α is adjusted by the irradiation angle adjustment unit 5. Thereafter, the standard samples 1 for the particle diameters of 10 nm, 20 nm, 30 nm, 50 nm, and 100 nm, respectively, are sequentially measured.

Figure 3:
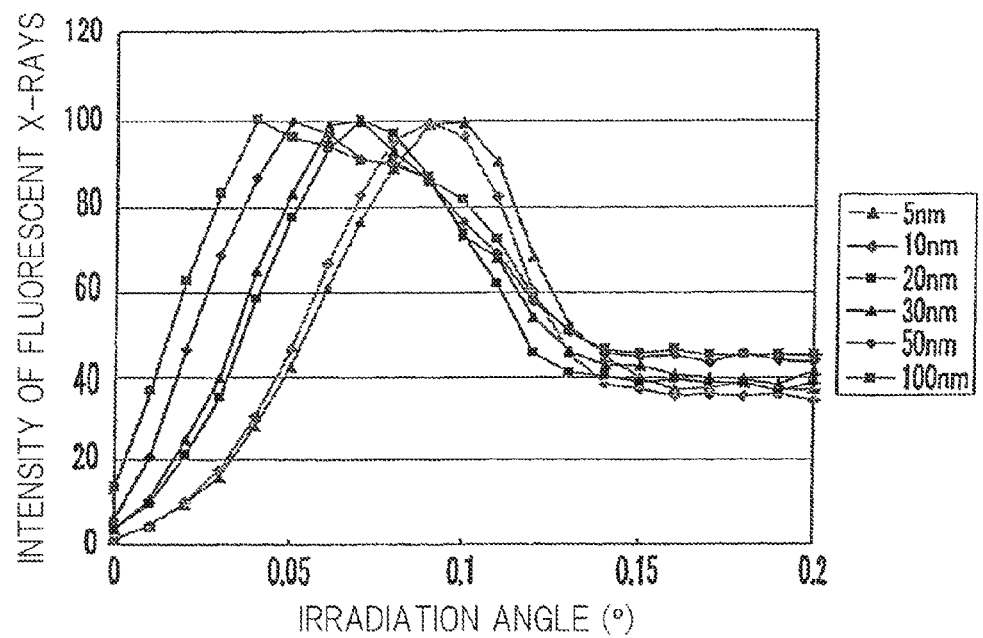
FIG. 3 illustrates a sample profile generated by the spectrometer.

The peak position calculation unit 11 measures, by using the detection unit 8, an intensity of the fluorescent X-rays 7 generated from each standard sample 1 each time the irradiation angle α is adjusted by the irradiation angle adjustment unit 5, generates a sample profile indicating change of the intensity of the fluorescent X-rays 7 against change of the irradiation angle α, and calculates a peak irradiation angle position at which the fluorescent X-rays 7 indicate the highest intensity in the sample profile. FIG. 3 shows the generated sample profile. In FIG. 3, the horizontal axis represents the irradiation angles, and the vertical axis represents intensities of the fluorescent X-rays. As shown in FIG. 3, as the particle diameter is increased, the peak irradiation angle position at which the fluorescent X-rays 7 indicate the highest intensity shifts toward a low irradiation angle side, and the half value width of the sample profile is increased.

Figure 4:
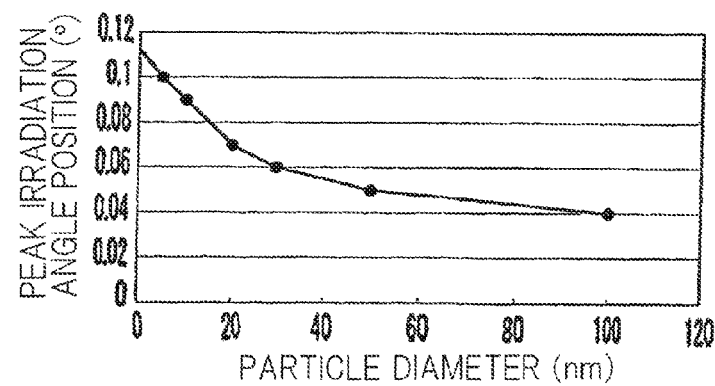
FIG. 4 illustrates a calibration curve generated by the spectrometer.

The particle diameter calibration curve generation unit 21 generates a calibration curve representing correlation between the peak irradiation angle positions calculated by the peak position calculation unit 11 and the particle diameters of the nanoparticles 1. FIG. 4 shows the generated calibration curve. In FIG. 4, the horizontal axis represents the particle diameters, and the vertical axis represents the peak irradiation angle positions. According to the calibration curve, an approximately average particle diameter of the nanoparticles 1 contained in the unknown sample 1 can be calculated.

Figure 5:
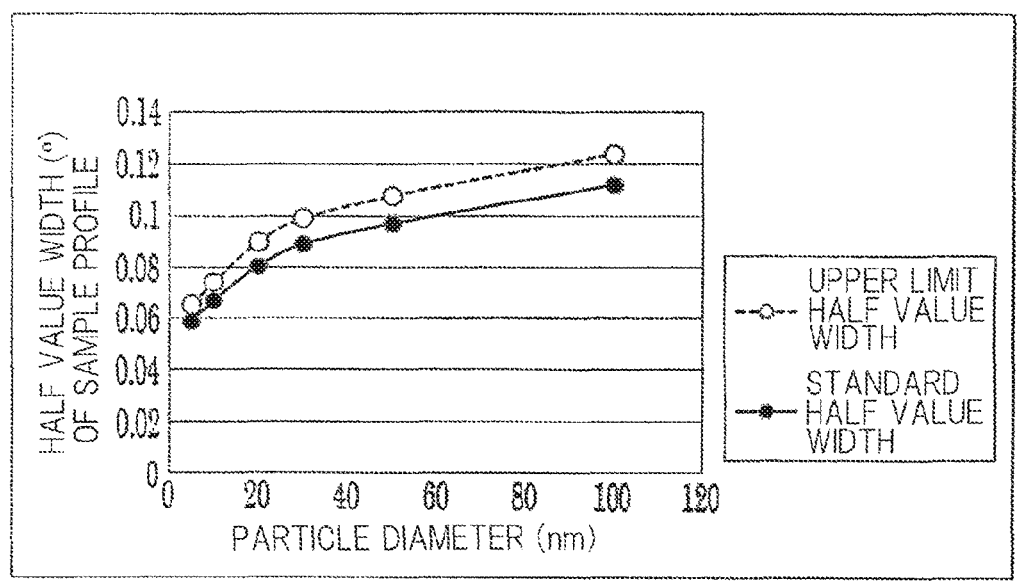
FIG. 5 illustrates upper limit half value widths and standard half value widths for the sample profile.

The half value width calculation unit 23 performs curve approximation for data of the sample profile shown in FIG. 3 except for data in a range of the critical angle of 0.11° and greater angles, calculates a half value width of the sample profile, of the standard sample 1, which is generated by the peak position calculation unit 11, obtains correlation between the particle diameters of the standard samples 1 and the standard half value widths calculated for the standard samples 1, and displays the correlation on the display unit 24. FIG. 5 shows the correlation. In FIG. 5, the horizontal axis represents the particle diameters (nm) and the vertical axis represents the half value widths (°) of the sample profiles of the standard samples 1, and the correlation between the standard half value widths and the particle diameters of the standard samples 1 is represented as a curve obtained by connecting black round plot points.

The sample profile of a sample in which particles having different particle diameters are mixed, is obtained by overlapping of the sample profiles of particles having the particle diameters, respectively. Therefore, the width of the sample profile is greater than that of the sample profile of a sample of particles having a uniform particle diameter, so that the particle diameter cannot be accurately measured. The previously obtained upper limit half value widths for the particle diameters of the standard samples 1 are inputted to the half value width calculation unit 23, whereby the half value width calculation unit 23 obtains correlation between the particle diameters of the standard samples 1 and the previously obtained upper limit half value widths for the particle diameters of the standard samples 1. The correlation is displayed by the display unit 24 as a curve obtained by connecting round outline plot points shown in FIG. 5. According to the upper limit half value width curve, whether or not the half value width calculated for the unknown sample 1 is less than or equal to the upper limit half value width, can be determined. Thus, a person who makes the measurement can sort the unknown sample 1 in which particles having different particle diameters are mixed and the particles do not have a predetermined particle diameter uniformity.

The upper limit half value width can be determined through calculation by simulation in which the sample profiles for a plurality of particle diameters, respectively, overlap each other, or on the basis of an actually measured value of a sample in which particles having a plurality of particle diameters are actually mixed. For example, when 20% by weight of particles having the particle diameter of 40 nm are mixed in particles having the particle diameter of 20 nm, the half value width is 0.09° according to calculation by simulation in which the sample profile of the particles having the diameter of 20 nm and the sample profile of the particles having the diameter of 40 nm overlap each other. Thus, the upper limit half value width for the particles having the particle diameter of 20 nm can be determined. The upper limit half value widths for particles having other particle diameters are similarly obtained.

Next, measurement is performed for an unknown sample 1A of multiple nanoparticles placed on the substrate 10, and the particle diameter calculation unit 22 calculates, as 12 nm, the particle diameter for the unknown sample 1A by applying the peak irradiation angle position calculated by the peak position calculation unit 11 for the unknown sample 1A, to the calibration curve (FIG. 4) generated by the particle diameter calibration curve generation unit 21. The calibration curve is generated by using the standard sample 1 of particles having the particle diameter of 5 nm, as the standard sample 1 of particles having the smallest particle diameter. However, if extrapolation is performed and the calibration curve is applied, the nanoparticles 1 having the particle diameter of 1 nm can be measured. Therefore, the X-ray fluorescence spectrometer can analyze the samples 1 of the nanoparticles having the particle diameters of 1 nm to 100 nm.

When the particle diameter for the unknown sample 1A is calculated as 12 nm, the half value width calculation unit 23 calculates, as 0.07°, the half value width of the sample profile of the unknown sample 1A. The half value width calculation unit 23 applies the particle diameter calculated as 12 nm for the unknown sample 1A to the curve, shown in FIG. 5, which is obtained by connecting the outline round plot points and represents the correlation with respect to the upper limit half value width, to obtain, as 0.075°, the upper limit half value width of the particle diameter of 12 nm. Then, the half value width calculation unit 23 determines whether or not the half value width, for the particle diameter of 12 nm, calculated as 0.07° is less than or equal to the upper limit half value width, for the particle diameter of 12 nm, obtained as 0.075°. The half value width, for the sample profile of the unknown sample 1A, calculated as 0.07° is less than or equal to the upper limit half value width of 0.075°. Therefore, the warning is not displayed on the display unit 24.

Next, measurement is performed for an unknown sample 1B, and the particle diameter calculation unit 22 calculates, as 20 nm, the particle diameter for the unknown sample 1B, and the half value width calculation unit 23 calculates, as 0.10°, the half value width of the sample profile of the unknown sample 1B. The half value width calculated as 0.10° is greater than the upper limit half value width of 0.09° for the particle diameter of 20 nm. Therefore, the half value width calculation unit 23 causes the display unit 24 to display the warning indicating that, for example, "a predetermined amount or more of particles having different particle diameters are contained". By such a warning, a person who makes the measurement can be made aware that a predetermined amount or more of particles having different particle diameters are contained in the unknown sample 1B. In this case, the predetermined amount is an amount of particles that have the particle diameter of 40 nm and are mixed in the particles having the particle diameter of 20 nm. Specifically, the predetermined amount is, for example, an amount corresponding to 20% by weight of the amount of the particles having the particle diameter of 20 nm. By the warning indicating that "a predetermined amount or more of particles having different particle diameters are contained", a person who makes the measurement is allowed to eliminate a sample in which a predetermined amount or more of particles having different particle diameters are contained, from the unknown samples 1 that are each a product which needs to have a predetermined uniform particle diameter, whereby the quality of the product can be improved.

As described above, the X-ray fluorescence spectrometer according to the first embodiment of the present invention, generates a calibration curve representing correlation between the peak irradiation angle positions and the particle diameters of the nanoparticles, applies the peak irradiation angle position of the unknown sample 1 to the calibration curve, and calculates the particle diameter of the nanoparticles placed on the substrate, whereby the measurement can be simply performed in a nondestructive manner with easy preprocessing.

An X-ray fluorescence spectrometer according to a second embodiment of the present invention will be described with reference to FIG. 6. The X-ray fluorescence spectrometer of the second embodiment includes an X-ray source 35 that is different from that of the X-ray fluorescence spectrometer of the first embodiment, and further includes an exciting line automatic selection unit 32 that controls the X-ray source 35, and an identification unit 31. The X-ray fluorescence spectrometer of the second embodiment is different from the X-ray fluorescence spectrometer of the first embodiment merely in that the X-ray fluorescence spectrometer of the second embodiment has the X-ray source 35, the exciting line automatic selection unit 32, and the identification unit 31. Only the difference in structure therebetween will be described. The exciting line automatic selection unit 32 and the identification unit 31 are included in the control unit 9. The identification unit 31 identifies an element of nanoparticles of the sample 1 on the basis of the output from the detection unit 8. The X-ray source 35 includes: two X-ray tubes, for example, a molybdenum X-ray tube 13 and a copper X-ray tube 33; and the spectroscopic device 4. The exciting line automatic selection unit 32 controls the X-ray tube selection unit (not shown) to select the X-ray tube that generates the exciting line corresponding to the identified element, and controls spectral angle adjustment unit (not shown) to set a spectral angle for the exciting line corresponding to the identified element.

Thus, the exciting line that corresponds to the element identified by the identification unit 31 and has advantageous excitation efficiency is automatically selected as the primary X-rays. For example, the molybdenum X-ray tube 13 is used for nanoparticles of gold (Au) or zinc (Zn), and the copper X-ray tube 33 is used for nanoparticles of silver (Ag) or titanium (Ti).

An operation performed by the X-ray fluorescence spectrometer according to the second embodiment of the present invention will be described. The identification unit 31 identifies an element of nanoparticles of an unknown sample 1C. In a case where the element of the nanoparticles 1 is identified as, for example, titanium, the exciting line automatic selection unit 32 automatically selects the copper X-ray tube 33 that generates the exciting line corresponding to titanium, and sets a spectral angle for the exciting line corresponding to titanium, in the spectroscopic device 4. When the exciting line is automatically selected, the unknown sample 1C is measured, and the particle diameter for the unknown sample 1C is calculated as 15 nm by using the calibration curve generated by previously measuring the standard sample 1 (standard sample for the same particle diameter as the particle diameter of the nanoparticle of gold) of the nanoparticles of silver, as in the X-ray fluorescence spectrometer according to the first embodiment of the present invention. The same exciting line, which is automatically selected, is used for measuring the standard sample 1 and the unknown sample 1C.

As described above, the X-ray fluorescence spectrometer according to the second embodiment of the present invention, can identify an element of the nanoparticles of the unknown sample 1, and generate the calibration curve by using exciting line corresponding to the identified element and the standard sample 1 that is suitable for the identified element, and calculate the particle diameters of the nanoparticles of the unknown sample 1, in addition to obtaining the same operation and effect as those of the X-ray fluorescence spectrometer according to the first embodiment of the present invention, whereby the particle diameter can be calculated with enhanced accuracy.

An X-ray fluorescence analyzing method according to a third embodiment of the present invention will be described. The X-ray source 3 that irradiates, with the primary X-rays 6, a sample 1 that is multiple nanoparticles placed on the substrate, the irradiation angle adjustment unit 5, such as a swivel stage, which adjusts an irradiation angle α at which the surface 10a of the substrate is irradiated with the primary X-rays 6, and the detection unit 8 that measures an intensity of the fluorescent X-rays 7 generated from the sample 1, are prepared. Next, a plurality of standard samples 1 each of which includes nanoparticles having a known uniform particle diameter, and among which the uniform particle diameter is different, are prepared. For example, the standard samples 1 in which the multiple nanoparticles 1 of gold on the substrate have particle diameters of 5 nm (nanometers), 10 nm, 20 nm, 30 nm, 50 nm, and 100 nm, respectively, are prepared. Firstly, the standard sample 1 for the particle diameter of 5 nm is irradiated with the primary X-rays 6, and the intensity of the fluorescent X-rays 7 generated from the standard sample 1 for the particle diameter of 5 nm is measured by the detection unit 8 each time the irradiation angle is adjusted by the irradiation angle adjustment unit 5. Thereafter, the standard samples 1 for the particle diameters of 10 nm, 20 nm, 30 nm, 50 nm, and 100 nm, respectively, are sequentially measured.

As described above, irradiation with the primary X-rays 6 is performed, and the intensity of the fluorescent X-rays 7 generated from each standard sample 1 is measured by the detection unit 8 each time the irradiation angle is adjusted by the irradiation angle adjustment unit 5. A sample profile representing change of the intensity of the fluorescent X-rays 7 against change of the irradiation angle is generated, and the peak irradiation angle position at which the fluorescent X-rays 7 indicate the highest intensity in the sample profile is obtained. The sample profile similar to that shown in FIG. 3 is obtained.

A particle diameter calibration curve representing correlation between the obtained peak irradiation angle positions and the particle diameters of the nanoparticles 1 is generated. The generated particle diameter calibration curve is a calibration curve similar to that shown in FIG. 4.

Next, measurement is performed for an unknown sample 1A of multiple nanoparticles placed on the substrate, similarly to the standard sample 1. The particle diameter for the unknown sample 1A is calculated as 12 nm by applying the obtained peak irradiation angle position for the unknown sample 1A, to the generated particle diameter calibration curve. The particle diameter calibration curve is generated by using the standard sample 1 of particles having the particle diameter of 5 nm, as the standard sample 1 of particles having the smallest particle diameter. However, if extrapolation is performed and the particle diameter calibration curve is applied, the nanoparticles 1 having the particle diameter of 1 nm can be also measured.

In the X-ray fluorescence analyzing method, the calibration curve representing correlation between the peak irradiation angle positions and the particle diameters of the nanoparticles is generated, and the peak irradiation angle position of the unknown sample 1 is applied to the calibration curve, whereby the samples 1 in which the nanoparticles on the substrate have particle diameters of 1 nm to 100 nm can be simply measured in a nondestructive manner with easy preprocessing. In the X-ray fluorescence analyzing method, the X-ray fluorescence spectrometer of the first embodiment can be used, but the peak position calculation unit 11, the particle diameter calibration curve generation unit 21, and the particle diameter calculation unit 22 may not be used.

An X-ray fluorescence analyzing method according to a fourth embodiment of the present invention will be described. The X-ray fluorescence analyzing method according to the fourth embodiment of the present invention is an analyzing method in which an element of nanoparticles of a sample 1 is identified, and exciting line corresponding to the identified element is selected as the primary X-rays, in the X-ray fluorescence analyzing method according to the third embodiment of the present invention. Therefore, process steps different from those of the X-ray fluorescence analyzing method according to the third embodiment will be described.

For example, a person who makes the measurement identifies an element of nanoparticles of an unknown sample 1C on the basis of the output from the detection unit 8. In a case where the element of the nanoparticles is identified as, for example, titanium, the person who makes the measurement selects the copper X-ray tube 33 that generates the exciting line corresponding to titanium, and sets, in the spectroscopic device 4, a spectral angle for the exciting line corresponding to titanium. When the exciting line has been selected, the standard sample 1 of nanoparticles of silver is measured to generate the particle diameter calibration curve, and the unknown sample 1C is measured to obtain, as 15 nm, the particle diameter for the unknown sample 1C, as in the X-ray fluorescence analyzing method according to the third embodiment of the present invention.

In the X-ray fluorescence analyzing method according to the fourth embodiment of the present invention, an element of the nanoparticles of the unknown sample 1 can be identified, and the calibration curve is generated by using the exciting line corresponding to the identified element, and the standard sample 1 that is suitable for the identified element, and the particle diameter of the nanoparticles of the unknown sample 1 is calculated, in addition to the same operation and effect as those by the X-ray fluorescence analyzing method according to the third embodiment of the present invention being obtained, whereby the particle diameter can be calculated with enhanced accuracy.

In the X-ray fluorescence spectrometers according to the first and the second embodiments of the present invention, a swivel stage is provided as the irradiation angle adjustment unit 5. However, the present invention is not limited thereto. The spectral angle of the spectroscopic device 4 may be adjusted to adjust the irradiation angle α at which the surface 10a of the substrate is irradiated with the primary X-rays 6. For the X-ray fluorescence spectrometer according to the second embodiment of the present invention and the X-ray fluorescence analyzing method according to the fourth embodiment of the present invention, the X-ray source that includes two X-ray tubes is described. However, an X-ray source that includes three or more X-ray tubes may be used. The X-ray source may be configured such that the exciting line is selected in one X-ray tube by changing the spectral angle of the spectroscopic device.

Although the present invention has been fully described in connection with the preferred embodiments thereof with reference to the accompanying drawings, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . sample
3 . . . X-ray source
5 . . . irradiation angle adjustment unit
6 . . . primary X-rays
7 . . . fluorescent X-rays
8 . . . detection unit
11 . . . peak position calculation unit
21 . . . particle diameter calibration curve generation unit
22 . . . particle diameter calculation unit
α . . . irradiation angle

What is claimed is:

1. An X-ray fluorescence spectrometer comprising:
an X-ray source configured to irradiate, with primary X-rays, a sample that is multiple nanoparticles placed on a substrate;
an irradiation angle adjustment unit configured to adjust an irradiation angle at which a surface of the substrate is irradiated with the primary X-rays;
a detection unit configured to measure an intensity of fluorescent X-rays generated from the sample;
a peak position calculation unit configured to measure, by using the detection unit, an intensity of the fluorescent X-rays generated from the sample each time the irradiation angle is adjusted by the irradiation angle adjustment unit, generate a sample profile representing change of the intensity of the fluorescent X-rays against change of the irradiation angle, and calculate a peak irradiation angle position at which the fluorescent X-rays indicate a highest intensity in the sample profile;
a particle diameter calibration curve generation unit configured to generate a calibration curve for a plurality of standard samples each of which includes nanoparticles having a known uniform particle diameter, and among which the uniform particle diameter is different, the calibration curve representing a correlation between the peak irradiation angle position calculated by the peak position calculation unit and the particle diameter of the nanoparticles; and
a particle diameter calculation unit configured to calculate a particle diameter of nanoparticles of an unknown sample by applying the peak irradiation angle position calculated for the unknown sample by the peak position calculation unit, to the calibration curve generated by the particle diameter calibration curve generation unit.

2. The X-ray fluorescence spectrometer as claimed in claim 1, comprising a display unit configured to display a warning when the particle diameter of the nanoparticles of the unknown sample is outside a predetermined particle diameter range of the calibration curve.

3. The X-ray fluorescence spectrometer as claimed in claim 1, comprising:
a half value width calculation unit configured to calculate a half value width of the sample profile generated by the peak position calculation unit; and
a display unit configured to display a warning when the half value width calculated for the unknown sample by the half value width calculation unit is greater than a predetermined upper limit half value width.

4. The X-ray fluorescence spectrometer as claimed in claim 1, comprising:
an identification unit configured to identify an element of nanoparticles of a sample, and
an exciting line automatic selection unit configured to automatically select, as the primary X-rays, exciting line corresponding to the element identified by the identification unit.

5. An X-ray fluorescence analyzing method comprising preparing: an X-ray source configured to irradiate, with primary X-rays, a sample that is multiple nanoparticles placed on a substrate; an irradiation angle adjustment unit configured to adjust an irradiation angle at which a surface of the substrate is irradiated with the primary X-rays; a detection unit configured to measure an intensity of fluorescent X-rays generated from the sample; and a plurality of standard samples each of which includes nanoparticles having a known uniform particle diameter, and among which the uniform particle diameter is different, irradiating each standard sample with the primary X-rays for which an irradiation angle is adjusted by using the irradiation angle adjustment unit, and measuring, by the detection unit, an intensity of fluorescent X-rays generated from the standard sample each time the irradiation angle is adjusted, generating a sample profile representing change of the intensity of the fluorescent X-rays against change of the irradiation angle, and calculating a peak irradiation angle position at which the fluorescent X-rays indicate a highest intensity in the sample profile, generating a particle diameter calibration curve representing a correlation between the peak irradiation angle position calculated for each standard sample, and the particle diameter of the nanoparticles, preparing an unknown sample, irradiating the unknown sample with the primary X-rays for which an irradiation angle is adjusted by using the irradiation angle adjustment unit, and measuring, by the detection unit, an intensity of fluorescent X-rays generated from the unknown sample each time irradiation is performed, generating a sample profile representing change of the intensity of the fluorescent X-rays against change of the irradiation angle, and calculating a peak irradiation angle position at which the fluorescent X-rays indicate a highest intensity in the sample profile, and calculating a particle diameter of nanoparticles of the unknown sample by applying the peak irradiation angle position calculated for the unknown sample, to the particle diameter calibration curve.

6. The X-ray fluorescence analyzing method as claimed in claim 5, wherein an element of nanoparticles of a sample is identified, and exciting line corresponding to the identified element is selected as the primary X-rays.

7. The X-ray fluorescence analyzing method as claimed in claim 5, wherein samples which include nanoparticles having particle diameters of 1 nm to 100 nm are analyzed.

* * * * *